United States Patent
Chaudhari et al.

(10) Patent No.: US 6,469,221 B1
(45) Date of Patent: Oct. 22, 2002

(54) PROCESS FOR THE CONVERSION OF 1, 4 BUTYNEDIOL TO 1, 4 BUTANEDIOL, OR A MIXTURE OF 1, 4 BUTENEDIOL AND 1,4 BUTANEDIOL

(75) Inventors: Raghunath Vitthal Chaudhari, Pune (IN); Chandrashekhar Vasant Rode, Pune (IN); Rengaswamy Jaganathan, Pune (IN); Manisha Madhukar Telkar, Pune (IN); Vilas Hari Rane, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/716,705

(22) Filed: Nov. 20, 2000

(51) Int. Cl.[7] .......................... C07C 27/00; C07C 29/00; C07C 31/18; C07C 33/00
(52) U.S. Cl. ....................................... 568/861; 568/857
(58) Field of Search ................................ 568/861, 857; 502/117, 118, 120

(56) References Cited

U.S. PATENT DOCUMENTS 5,650,546 A * 7/1997 Chaudhari et al. .......... 585/269

FOREIGN PATENT DOCUMENTS

CA 2260810 A * 4/1998

* cited by examiner

Primary Examiner—Johann Richter
Assistant Examiner—Elvis O. Price
(74) Attorney, Agent, or Firm—Ladas & Parry

(57) ABSTRACT

The present invention relates to a process for the conversion of 1,4 butynediol to 1,4 butanediol or a mixture of 1,4 butanediol and 1,4 butenediol comprising hydrogenating an aqueous solution of 1,4 butynediol using platinum supported $CaCO_3$ catalyst at a temperature in the range of 20–190° C. under a hydrogen pressure in the range between 5–100 bar and collecting the product by any known method.

11 Claims, No Drawings

PROCESS FOR THE CONVERSION OF 1, 4 BUTYNEDIOL TO 1, 4 BUTANEDIOL, OR A MIXTURE OF 1, 4 BUTENEDIOL AND 1,4 BUTANEDIOL

FIELD OF THE INVENTION

The present invention relates to a process for the conversion of 1, 4 butynediol to 1, 4 butanediol, or a mixture of 1, 4 butenediol and 1,4 butanediol. More particularly, the present invention relates to a process for the preparation of 1, 4 butanediol, or a mixture of 1, 4 butenediol and 1,4 butanediol (in different compositions) in a fixed bed reactor using a platinum supported calcium carbonate catalyst.

BACKGROUND OF THE INVENTION 1, 4 butenediol is a useful intermediate in the production of pesticide, insecticide and vitamin B6. Being an unsaturated diol it can be used in the synthesis of many organic products such as tetrahydrofuran, n-methyl pyrrolidione, γ-butyrolactone, etc. It is also used as an additive in the paper industry, as a stabiliser in resin manufacture, as a lubricant for bearing systems and in the synthesis of allyl phosphates. 1, 4 butanediol also has a variety of applications such as in the preparation of polyurethane foams and other polyesters as well as in the preparation of tetrahydrofuran.

Prior art discloses the use of a number of catalysts for the manufacture of 1, 4 butenediol by the hydrogenation of 1, 4 butynediol. Most of the prior art patents are based on a combination of palladium with one or more mixed compounds of copper, all zinc, calcium, cadmium, lead, alumna, mercury, tellurium, gallium, etc. GB A 871804 describes the selective hydrogenation of acetylinic compound in a suspension method using a Pd catalyst which has been treated with the salt solutions of Zn, Cd, Hg, Ga, Th, In, or Ga. The process is carried out at milder conditions with 97% selectivity for cis 1,2-butenediol and 3% to the trans form. Moreover, additional amines are used in this process.

U.S. Pat. No. 2,681,938 discloses the use of a Lindlar catalyst (lead doped Pd catalyst), for the selective hydrogenation of acetylinic compounds. The drawback of this process is the use of additional amines such as pyridine to obtain good selectivity for 1, 4 butenediol.

German patent DE 1, 213, 839 describes a Pd catalyst doped with Zn salts and ammonia for the partial hydrogenation of acetylinic compounds. However, this catalyst suffers from the drawback of short lifetime due to poisoning.

German patent application DE-A 2, 619, 660 describes the use of Pd/Al$_2$O$_3$ catalyst that has been treated with carbon monoxide for the hydrogenation of butynediol in an inert solvent. The disadvantage of this catalyst is that the catalyst is treated with carbon monoxide gas which is highly toxic and difficult to handle.

U.S. Pat. No. 2,961,471 discloses a Raney nickel catalyst useful for the partial hydrogenation of 1, 4 butynediol. The catalyst of this process gives a low selectivity for 1, 4 butenediol.

U.S. Pat. No. 2,953,604 describes a Pd containing charcoal and copper catalyst for the reduction of 1,4 butynediol to 1,4 butenediol with 81% selectivity for 1,4 butenediol. However, this process results in the formation of a large number of side products and is therefore undesirable.

U.S. Pat. No. 4,001,344 discloses the use of palladium mixed with γ- Al$_2$O$_3$ along with both zinc and cadmium or either zinc or cadmium together with bismuth or tellurium for the preparation of 1,4 butenediol by the selective hydrogenation of 1, 4 butynediol. However, a large number of residues are formed (7.5–12%) which lowers the selectivity of 1,4 butenediol to 88%.

U.S. Pat. Nos. 5,521,139 and 5,278,900 describes the use of a Pd containing catalyst for the hydrogenation of 1,4 butynediol to prepare 1,4 butenediol. The catalyst used is a fixed bed catalyst prepared by applying Pd and Pb or Pd and Cd successively by vapor deposition or sputtering to a metal gauze or a metal foil acting as a support. In this process also the selectivity obtained for cis 1,4 butenediol is 98%. The disadvantage of this process is that a trans butenediol with residues are also obtained.

Prior art also discloses a number of catalysts for the preparation of 1,4 butanediol by the hydrogenation of 1,4 butynediol.

Most prior art patents are based on a combination of palladium or nickel with one or more of mixed compounds of copper, manganese, molybdenum, zirconium, etc.

U.S. Pat. No. 3,449,445 discloses a process for the hydrogenation of 1,4 butynediol to 1,4 butanediol with good yield using a catalyst containing Ni, Cu, and Mn on silicon dioxide. The disadvantage of this process is that when 1,4 butanediol is prepared by this process on an industrial scale, silicon dioxide is deposited in the heat exchangers and pipelines, the removal of which is a highly laborious procedure.

De OS 2,536, 276 describes the preparation of 1,4 butanediol by the hydrogenation of 1,4 butynediol using the oxides of Ni, Cu, Mo, and Mn.

U.S. Pat. No. 5,015,788 describes a process for the hydrogenation of acetylinic compounds using a catalyst containing oxides of Ni, Cu, Mo and Zr. While the process shows promising results at high temperature of upto 250° C. and pressure of 150 bar, side products such as butanol, 2-methyl 1,4 butanol, γ-hydroxylactone, 4-hydroxybutaraldehyde, etc. are formed.

EP 337572 discloses a process for the preparation of alkanediols using H in the presence of cationic Pd, a corresponding anion and bidentate ligands with high selectivity for 1,4 butanediol. However, this process suffers from a major drawback in that side products such as γ-hydroxy butyraldehyde are formed and expensive bidentate ligands need to be used.

EP 295435 describes a process for the preparation of 1,4 butanediol with high selectivity using a nickel acetate catalyst with the addition of C ≧2 organic acids at high temperatures (185–195° C.) and hydrogen pressure (250 bar). While the selectivity for 1,4 butanediol is good, unwanted side products such as n-butanol, hydroxybutaraldehyde, 2-methyl 1,4 butanediol, acetal and the like are formed. Moreover, the process is carried out at a very high temperature and H$_2$ pressure.

All the above processes for the hydrogenation of butynediol to butenediol or butanediol suffer from disadvantages such as high temperatures, pressures, formation of side products. The formation of side products and residues affect the efficiency of the process and the recovery of pure 1,4 butenediol and butanediol is difficult. An additional drawback is that the catalysts used for these processes contain more than two metals along with other promoters such as organic amines. Their preparation is cumbersome. All the reported processes also do not give complete selectivity for the desired products either 1,4 butenediol or 1,4 butanediol. The catalysts also suffer from fast deactivation due to poisoning.

The prior art literature shows that the catalysts used for the hydrogenation of 1,4 butynediol are mainly palladium or nickel based catalysts. There is no disclosure or report on the use of platinum based catalysts for the hydrogenation of 1,4 butynediol to prepare 1,4 butanediol or a mixture of 1,4 butenediol and 1,4 butanediol (in various compositions).

It is therefore important to obtain and/or develop catalysts that overcome the disadvantages of prior art catalysts used in the hydrogenation of 1,4 butynediol to 1,4 butanediol or a mixture of 1,4 butenediol and 1,4 butanediol (in various compositions) enumerated above.

OBJECTS OF THE INVENTION

The main object of the invention is to provide a process for the preparation of diols, particularly 1, 4 butanediol or mixtures of 1,4 butenediol and 1,4 butanediol (in varying proportions) by the hydrogenation of 1,4 btuynediol that is cheap and efficient.

It is another object of the invention to provide a process for the preparation of 1,4 butanediol with 100% selectivity.

It is another object of the invention to provide a process for the preparation of mixtures of 1,4 butenediol and 1,4 butanediol in vrying proportions under mild reaction conditions.

SUMMARY OF THE INVENTION

Accordingly the present invention provides a process for the conversion of 1, 4 butynediol to 1, 4 butanediol, or a mixture of 1, 4 butenediol and 1,4 butanediol comprising hydrogenating aqueous solution of 1,4 butynediol using platinum supported $CaCO_3$ catalyst at a temperature in the range of 20–190° C. under a hydrogen pressure in the range between 5–100 bar and collecting the product by any conventional method.

In one embodiment of the invention, the concentration of 1,4 butynediol in aqueous medium is in the range of 10–70%, preferably 15–50%.

In another embodiment of the invention, the gas hourly space velocity (GHSV) is in the range of 500–12000 $h^{-1}$, preferably 1000–10000 $h^{-1}$.

In another embodiment of the invention, the liquid hourly space velocity (LHSV) is in the range of 0.05–15 $h^{-1}$, preferably 0.1–10 $h^{-1}$.

In another embodiment of the invention, the process is carried out under hydrogen pressure of 10–80 bar.

In a further embodiment of the invention, the process is carried out at a temperature in the range of 40–160° C.

In another embodiment of the invention, the catalyst is run for 200 hours and the turn over number (TON) is $7.24 \times 10^4$.

In another embodiment of the invention, the catalyst is of the of the general formula AB(y) wherein A is a support comprising of carbonate of calcium, B is platinum and y=0.2 to 10%.

DETAILED DESCRIPTION OF THE INVENTION

In the present invention the catalyst is prepared by impregnating platinum supported $CaCO_3$ in a basic medium (pH=7–12), stirred in water and heated in the temperature range of 60–120° C., preferably 70–90° C. The mixture is then reduced by adding a conventional reducing agent such as formaldehyde. The solution is stirred, filtered, washed and dried at a temperature in the range of 100–250° C., preferably 140–200° C. in static air for a period in the range of 5–12 hours.

The hydrogenation catalyst used is of the general formula AB(y) wherein A is a support comprising of a salt of a Group II A metal, B is platinum and y=0.2 to 10%.

The catalyst used in the invention is prepared by:
i. dissolving a platinum precursor in a mineral acid by stirring at a temperature in the range between 60° C. to 120° C.;
ii. diluting the above solution by adding water;
iii. adjusting the pH of the solution to the range of 8–12 by the addition of a base,
iv. adding a support to the above solution;
v. heating the mixture to a temperature in the range of 60° C. to 120° C.;
vi. reducing the above mixture using a conventional reducing agent;
vii. separating the catalyst formed by any conventional method;
viii. washing and drying the product to obtain the desired catalyst.

The platinum precursor is a salt of platinum selected from the group comprising of acetate, bromide, and chloride of platinum. The support is a salt of a Group II A metal selected from the group comprising of acetate, nitrate, chloride, carbonates of magnesium, calcium, and barium. The base used may be selected from the group comprising of sodium carbonate, potassium carbonate, potassium hydroxide, and sodium hydroxide.

The reducing agent used is selected from the group comprising of hydrazine hydrate, hydrogen containing gas, and formaldehyde.

Hydrogenation was carried out in a single tube reactor of 19 mm diameter. In a typical experiment the catalyst was charged approximately in the middle portion of the reactor tube. The space above and below the catalyst was packed with inert carborundum beads. The reactor was heated by an electric furnace. The liquid feed 1,4 butynediol and hydrogen were introduced near the top of the reactor. The inert zone over the top of the catalyst served as a preheater for the reactants. The product stream leaving the reactor is cooled to condense the liquid products. The products are analysed using a gas chromatograph after the reaction. It is noted that the selectivity of the process at milder process conditions is 100%.

The present invention is described below by way of examples. However, the following examples are illustrative and should not be construed as limiting the scope of the invention.

EXAMPLE 1

Preparation of 1% $Pt/CaCO_3$ Catalyst 0.17 gms of platinum chloride was dissolved in 4 ml of hydrochloric acid and stirred at 80° C. till the platinum chloride was completely dissolved. The resultant solution was diluted by adding 50 ml of water and stirring for 2 hours, the pH being maintained between 9–10 by the addition of sodium hydroxide. To the diluted solution, 10.03 gins of calcium carbonate was added and the mixture heated at 80° C. for 1 hour. The mixture was then reduced by the addition of formaldehyde (3 ml), stirred for 45 minutes, filtered and washed with water till the solution is alkaline free. The catalyst was then dried at 150° C. for 10 hours.

EXAMPLE 2

Performance of 1% $Pt/CaCO_3$ Catalyst (10 gms)in the Hydrogenation of 1,4 Butynediol to 1,4 Butenediol and 1,4 Butanediol This example illustrates the performance of 1% $Pt/CaCO_3$ catalyst (10 gms) in the hydrogenation of 1,4 butynediol to 1,4 butenediol and 1,4 butanediol The reaction was carried out in a fixed bed reactor in the presence of the catalyst according to the procedure described hereinabove.

The reaction was carried out at the following reaction conditions:

| | |
|---|---|
| Concentration of 1,4 butynediol in water | 20% |
| Weight of catalyst | 10.0 gms |
| Temperature | 50°, 75° and 100° C. |
| $H_2$ pressure | 25 bar |
| $H_2$ flow | 10 NL/hour |
| Liquid flow | 10 cm$^3$/hour |

The following results are obtained:

| Temperature (° C.) | 50 | 75 | 100 |
|---|---|---|---|
| 1,4 butynediol conversion (%) | 35.0 | 53.7 | 50.2 |
| Selectivity for 1,4 butanediol (%) | 51.0 | 54.1 | 55.0 |
| Selectivity for 1,4 butenediol (%) | 49.0 | 45.9 | 45.0 |

EXAMPLE 3

The reaction was carried out at the following reaction conditions:

| | |
|---|---|
| Concentration of 1,4 butynediol in water | 20% |
| Weight of catalyst | 10.0 gms |
| Temperature | 100° C. |
| $H_2$ pressure | 25 bar |
| $H_2$ flow | 10, 20, 30 and 60 NL/hour |
| Liquid flow | 10 cm$^3$/hour |

The following results are obtained:

| $H_2$ flow (NL/hr) | 10 | 20 | 30 | 60 |
|---|---|---|---|---|
| 1,4 butynediol conversion (%) | 50.2 | 59.1 | 56.5 | 54.4 |
| Selectivity for 1,4 butanediol (%) | 55.0 | 60.6 | 30.0 | 30.2 |
| Selectivity for 1,4 butenediol (%) | 45.0 | 39.4 | 70.0 | 69.8 |

EXAMPLE 4

The reaction was carried out at the following reaction conditions:

| | |
|---|---|
| Concentration of 1,4 butynediol in water | 20% |
| Weight of catalyst | 10.0 gms |
| Temperature | 75° C. |
| $H_2$ pressure | 25 bar |
| $H_2$ flow | 10, 20, 30 and 60 NL/hour |
| Liquid flow | 10 cm$^3$/hour |

The following results are obtained:

| $H_2$ flow (NL/hr) | 10 | 20 | 30 | 60 |
|---|---|---|---|---|
| 1,4 butynediol conversion (%) | 53.7 | 21.7 | 20.1 | 20.1 |
| Selectivity for 1,4 butanediol (%) | 54.0 | 29.8 | 30.9 | 30.0 |
| Selectivity for 1,4 butenediol (%) | 46.0 | 70.2 | 69.1 | 70.0 |

EXAMPLE 5

The reaction was carried out at the following reaction conditions:

| | |
|---|---|
| Concentration of 1,4 butynediol in water | 20% |
| Weight of catalyst | 10.0 gms |
| Temperature | 50° C. |
| $H_2$ pressure | 25 bar |
| $H_2$ flow | 10, 20, 30 and 60 NL/hour |
| Liquid flow | 10 cm$^3$/hour |

The following results are obtained:

| $H_2$ flow (NL/hr) | 10 | 20 | 30 | 60 |
|---|---|---|---|---|
| 1,4 butynediol conversion (%) | 35.0 | 21.4 | 19.2 | 18.2 |
| Selectivity for 1,4 butanediol (%) | 51.0 | 65.0 | 64.3 | 62 |
| Selectivity for 1,4 butenediol (%) | 49.0 | 35.0 | 35.7 | 38 |

EXAMPLE 6

The reaction was carried out at the following reaction conditions:

| | |
|---|---|
| Concentration of 1,4 butynediol in water | 20% |
| Weight of catalyst | 10.0 gms |
| Temperature | 100° C. |
| $H_2$ pressure | 25 bar |
| $H_2$ flow | 10 NL/hour |
| Liquid flow | 10, 20 and 40 cm$^3$/hour |

The following results are obtained:

| Liquid flow (cm$^3$/hour) | 10 | 20 | 40 |
|---|---|---|---|
| 1,4 butynediol conversion (%) | 50.2 | 39.6 | 16.0 |
| Selectivity for 1,4 butanediol (%) | 55.0 | 69.0 | 27.9 |
| Selectivity for 1,4 butenediol (%) | 45.0 | 31.0 | 72.1 |

EXAMPLE 7

The reaction was carried out at the following reaction conditions:

| | |
|---|---|
| Concentration of 1,4 butynediol in water | 20% |
| Weight of catalyst | 10.0 gms |
| Temperature | 75° C. |
| $H_2$ pressure | 25 bar |

-continued

| | |
|---|---|
| H₂ flow | 10 NL/hour |
| Liquid flow | 10, 20 and 40 cm³/hour |

The following results are obtained:

| Liquid flow (cm³/hour) | 10 | 20 | 40 |
|---|---|---|---|
| 1,4 butynediol conversion (%) | 53.7 | 28.3 | 23.5 |
| Selectivity for 1,4 butanediol (%) | 54.1 | 24.0 | 24.6 |
| Selectivity for 1,4 butenediol (%) | 46.0 | 76.0 | 75.6 |

EXAMPLE 8

The reaction was carried out at the following reaction conditions:

| | |
|---|---|
| Concentration of 1,4 butynediol in water | 20% |
| Weight of catalyst | 20.0 gms |
| Temperature | 50° C. |
| H₂ pressure | 15, 25, 40 and 60 bar |
| H₂ flow | 10 NL/hour |
| Liquid flow | 10 cm³/hour |

The following results are obtained:

| H₂ pressure (bar) | 15 | 25 | 40 | 60 |
|---|---|---|---|---|
| 1,4 butynediol conversion (%) | 32.1 | 50.9 | 62.6 | 90.0 |
| Selectivity for 1,4 butanediol (%) | 60.1 | 60.7 | 57.8 | 62.0 |
| Selectivity for 1,4 butenediol (%) | 39.9 | 39.3 | 42.2 | 38.0 |

EXAMPLE 9

The reaction was carried out at the following reaction conditions:

| | |
|---|---|
| Concentration of 1,4 butynediol in water | 20% |
| Weight of catalyst | 20.0 gms |
| Temperature | 75° C. |
| H₂ pressure | 15, 25, 40 and 60 bar |
| H₂ flow | 10 NL/hour |
| Liquid flow | 10 cm³/hour |

The following results are obtained:

| H₂ pressure (bar) | 15 | 25 | 40 | 60 |
|---|---|---|---|---|
| 1,4 butynediol conversion (%) | 49.6 | 70.9 | 62.6 | 100 |
| Selectivity for 1,4 butanediol (%) | 52.4 | 52.8 | 57.8 | 66.6 |
| Selectivity for 1,4 butenediol (%) | 47.6 | 47.2 | 42.2 | 33.5 |

EXAMPLE 10

The reaction was carried out at the following reaction conditions:

| | |
|---|---|
| Concentration of 1,4 butynediol in water | 20% |
| Weight of catalyst | 20.0 gms |
| Temperature | 100° C. |
| H₂ pressure | 15, 25 and 40 bar |
| H₂ flow | 10 NL/hour |
| Liquid flow | 10 cm³/hour |

The following results are obtained:

| H₂ pressure (bar) | 15 | 25 | 40 |
|---|---|---|---|
| 1,4 butynediol conversion (%) | 74.7 | 92.8 | 100 |
| Selectivity for 1,4 butanediol (%) | 52.5 | 55.2 | 55.5 |
| Selectivity for 1,4 butenediol (%) | 47.5 | 45.1 | 44.5 |

EXAMPLE 11

The reaction was carried out at the following reaction conditions:

| | |
|---|---|
| Concentration of 1,4 butynediol in water | 20% |
| Weight of catalyst | 20.0 gms |
| Temperature | 50°, 75° and 100° C. |
| H₂ pressure | 25 bar |
| H₂ flow | 10 NL/hour |
| Liquid flow | 20 cm³/hour |

The following results are obtained:

| Temperature (° C.) | 50 | 75 | 100 |
|---|---|---|---|
| 1,4 butynediol conversion (%) | 16.8 | 18.3 | 53.4 |
| Selectivity for 1,4 butanediol (%) | 48.2 | 50.0 | 39.5 |
| Selectivity for 1,4 butenediol (%) | 51.8 | 50.0 | 60.5 |

EXAMPLE 12

The reaction was carried out at the following reaction conditions:

| | |
|---|---|
| Concentration of 1,4 butynediol in water | 20% |
| Weight of catalyst | 20.0 gms |
| Temperature | 100° C. |
| H₂ pressure | 25 bar |
| H₂ flow | 20, 40 and 60 NL/hour |
| Liquid flow | 10 cm³/hour |

The following results are obtained:

| H₂ flow (NL/hr) | 20 | 40 | 60 |
|---|---|---|---|
| 1,4 butynediol conversion (%) | 80.5 | 78.6 | 86.5 |
| Selectivity for 1,4 butanediol (%) | 44.2 | 49.4 | 43.3 |
| Selectivity for 1,4 butenediol (%) | 55.9 | 50.4 | 57.1 |

EXAMPLE 13

This example illustrates the performance or the use of the 1% Pt/CaCO₃ catalyst (5 gms) in the hydrogenation of 1,4 butynediol to 1,4butenediol and 1,4 butanediol.

The reaction was carried out in a fixed bed reactor in the presence of the catalyst according to the procedure described hereinabove.

The reaction was carried out at the following reaction conditions:

| | |
|---|---|
| Concentration of 1,4 butynediol in water | 20% |
| Weight of catalyst | 5.0 gms |
| Temperature | 75° C. |
| $H_2$ pressure | 25 bar |
| $H_2$ flow | 10 NL/hour |
| Liquid flow | 10 and 20 $cm^3$/hour |

The following results are obtained:

| Liquid flow ($cm^3$/hour) | 10 | 20 |
|---|---|---|
| 1,4 butynediol conversion (%) | 13.0 | 8.3 |
| Selectivity for 1,4 butanediol (%) | 40.2 | 55.0 |
| Selectivity for 1,4 butenediol (%) | 59.8 | 45.0 |

EXAMPLE 14

This example illustrates the performance or the use of the 1% Pt/$CaCO_3$ catalyst (30 gms) in the hydrogenation of 1,4 butynediol to 1,4butanediol and 1,4 butanediol.

The reaction was carried out in a fixed bed reactor in the presence of the catalyst according to the procedure described hereinabove.

The reaction was carried out at the following reaction conditions:

| | |
|---|---|
| Concentration of 1,4 butynediol in water | 20% |
| Weight of catalyst | 30.0 gms |
| Temperature | 125° C. |
| $H_2$ pressure | 25 and 40 bar |
| $H_2$ flow | 10 NL/hour |
| Liquid flow | 10 $cm^3$/hour |

The following results are obtained:

| $H_2$ pressure (bar) | 25 | 40 |
|---|---|---|
| 1,4 butynediol conversion (%) | 100 | 100 |
| Selectivity for 1,4 butanediol (%) | 95.8 | 96.2 |
| Selectivity for 1,4 butenediol (%) | 4.2 | 3.8 |

EXAMPLE 15

The reaction was carried out at the following reaction conditions:

| | |
|---|---|
| Concentration of 1,4 butynediol in water | 20% |
| Weight of catalyst | 30.0 gms |
| Temperature | 140° C. |
| $H_2$ pressure | 25 bar |
| $H_2$ flow | 10 NL/hour |
| Liquid flow | 10 $cm^3$/hour |

The following results are obtained:

| | |
|---|---|
| 1,4 butynediol conversion (%) | 100 |
| Selectivity for 1,4 butanediol (%) | 100 |

Advantages of the Invention

1. The catalyst of the invention is useful for the selective hydrogenation of 1, 4 butynediol to 1, 4 butanediol or 1, 4 butenediol and 1,4 butanediol (in various compositions) without poisoning.
2. Selective hydrogenation of 1, 4 butynediol to 1, 4 butanediol is achieved in a continuous operation using 1% Pt/$CaCO_3$ catalyst without addition of any promoter or ammonia in the reaction mixture.
3. Substantially complete conversion of 1, 4 butynediol to 1, 4 butenediol with almost 100% selectivity to cis 1, 4 butenediol is obtained at milder process conditions.
4. The separation of the product 1, 4 butanediol in pure form is achieved easily by the removal of the catalyst from the reaction mixture.
5. The product mixture of 1,4 butenediol and 1,4 butanediol is obtained without any side product formation. Also, the composition of the product mixture can be varied by changing the reaction conditions.

We claim:

1. A process for the conversion of 1,4-butynediol to 1,4-butanediol or a mixture of 1,4-butenediol and 1,4-butanediol comprising hydrogenating an aqueous solution of 1,4-butynediol using a platinum supported $CaCO_3$ catalyst wherein the platinum is in the zero oxidation state at a temperature in the range of 20–190° C. under a hydrogen pressure in the range between 5–100 bar and collecting the product by known method.

2. A process as claimed in claim 1, wherein the concentration of 1,4-butynediol in aqueous medium is in the range of 10–70%.

3. A process as claimed in claim 2 wherein the concentration of 1,4 butynediol in aqueous medium is in the range of 15–50%.

4. A process as claimed in claim 1, wherein the conversion of 1,4-butynediol to 1,4-butanediol or a mixture of 1,4-butenediol and 1,4-butanediol is carried out at a gas hourly space velocity (GHSV) in the range of 500–12000 $h^{-1}$.

5. A process as claimed in claim 4 wherein the gas hourly space velocity (GHSV) is in the range of 1000–10000 $h^{-1}$.

6. A process as claimed in claim 1 wherein the conversion of 1,4-butynediol to 1,4-butanediol or a mixture of 1,4-butenediol and 1,4-butanediol is carried out at a liquid hourly space velocity (LHSV) in the range of 0.05–15 $h^{-1}$.

7. A process as claimed in claim 6 wherein the liquid hourly space velocity (LHSV) is in the range of 0.1–10 $h^{-1}$.

8. A process as claimed in claim 1 wherein the process is carried out under hydrogen pressure of 10–80 bar.

9. A process as claimed in claim 1 wherein the process is carried out at a temperature in the range of 40–160° C.

10. A process as claimed in claim 1 wherein the catalyst is run for 200 hours and the turn over number (TON) is 7.24×104.

11. A process as claimed in claim 1 wherein the catalyst is of the of the general formula AB(y) wherein A is a support comprising of carbonate of calcium, B is platinum and y=0.2 to 10%.

* * * * *